(12) United States Patent
Wun et al.

(10) Patent No.: US 6,171,587 B1
(45) Date of Patent: Jan. 9, 2001

(54) ANTIBODIES TO TISSUE FACTOR INHIBITOR

(75) Inventors: Tze Chein Wun, Ballwin; Kuniko K. Kretzmer, Wildwood; George J. Broze, Jr., St. Louis, all of MO (US)

(73) Assignee: G. D. Searle and Company, Chicago, IL (US)

( * ) Notice: Under 35 U.S.C. 154(b), the term of this patent shall be extended for 0 days.

(21) Appl. No.: 09/054,782

(22) Filed: Apr. 3, 1998

Related U.S. Application Data

(63) Continuation of application No. 08/463,323, filed on Jun. 5, 1995, now Pat. No. 5,849,875, which is a continuation of application No. 08/355,351, filed on Dec. 13, 1994, now abandoned, which is a continuation of application No. 07/566,280, filed on Aug. 13, 1990, now abandoned, which is a division of application No. 07/123,753, filed on Nov. 23, 1987, now Pat. No. 4,966,852, which is a continuation-in-part of application No. 07/077,366, filed on Jul. 23, 1987, now abandoned.

(51) Int. Cl.[7] .................... C07K 16/24; A61K 39/395
(52) U.S. Cl. ................... 424/139.1; 530/387.1; 530/387.9; 530/388.1; 530/389.2
(58) Field of Search ............... 530/387.1, 387.9, 530/388.1, 388.23, 389.2; 435/325, 326, 331, 337; 424/130.1, 139.1, 145.1

(56) References Cited

U.S. PATENT DOCUMENTS 4,831,118 * 5/1989 Zimmerman et al. .............. 530/383

OTHER PUBLICATIONS

Hjort, Scan. J. Clin. Lab. Invest., 9(suppl. 27), p. 76–97, (1957).
Broze et al., Blood, 69. 150–155, (1987).
Sanders et al., Blood, 66, 204–212 (1985).
Broze et al., Proc. Natl. Acad. Sci. USA 84, 1886–1890 (1987).
Proudfoot et al., Nature, 252, 359–362 (1981).
Von Heijne, Eur. J. Biochem. 123, 17–21 (1983).
Von Heijne, J. Mol. Biol. 184, 99–105 (1985).
Kozak, Cell, 44, 283–292, (1986).
Henikoff, Gene, 28, 351–359 (1984).
Lipman & Pearson, Science 227, 1435–1441 (1985).
Sanger et al., Proc. Natl. Acad. Sci. USA 70(4), 1209–1213 (1973).
Maniatis et al., Molecular Cloning: A Laboratory Manual, Cold Spring Harbor Laboratory, Cold Spring Harbor, New York, (1982).
Thomas, Methods Enzymol. 100, 255–266 (1983).
Lizardi & Engelberg, Anal. Biochem. 98, 116–122 (1979).
Wun & Kretzmer, FEBS Lett. 1, 11–16 (1987).
Kidera et al., J. Prot. Chem. 4, 23–55 (1985).
Young & Davis, Proc. Natl. Acad. Sci. USA, 80, 1194–1198 (1983).

* cited by examiner

*Primary Examiner*—Prema Mertz
(74) *Attorney, Agent, or Firm*—Verne A. Luckow

(57) ABSTRACT

A cDNA clone having a base sequence for human tissue factor inhibitor (TFI) has been developed and characterized and the amino acid sequence of the TFI has been determined. Antibodies having a binding region specific to human tissue factor inhibitor are disclosed.

6 Claims, 7 Drawing Sheets

Figure 1:
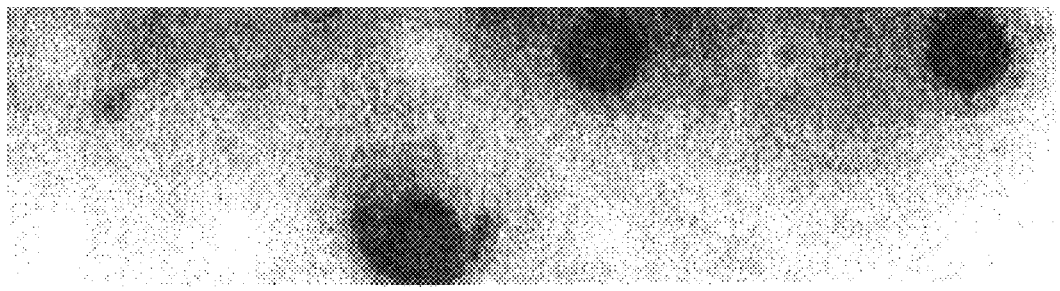

```
  1  GGC GGG TCT GCT TCT AAA AGA AGT AGA GAA GAT AAA TCC TGT CTT CAA TAC CTG GAA GGA AAA ACA AAA TAA CCT CAA CTC CGT TTT
                                                                                                        +1
 91  GAA AAA AAC ATT CCA ACT TTC ATC AGA GAT TTT ACT TAG ATG ATT TAC ACA ATG AAG AAA GTA CAT GCA CTT TGG GCT TCT GTA TGC   16
                                                          Met Ile Tyr Thr Met Lys Lys Val His Ala Leu Trp Ala Ser Val Cys

181  CTG CTG CTT AAT CTT GCC CCT CCT CTT AAT GCT CCT GAG GAA GAA CAC ACA ATT ATC ACA GAT TTT TTC AAT ATT TTC ACT           46
     Leu Leu Leu Asn Leu Ala Pro Pro Leu Asn Ala Pro Glu Glu Glu His Thr Ile Ile Thr Asp Phe Phe Asn Ile Phe Thr

271  CTG AAA CTT ATG CAT TCA TTT TGT GCA TTC AAG GCG GAT GAT GGC CCA TGT AAA GCA ATC ATG AAA AGA TTT TTC ACA AGA           76
     Leu Lys Leu Met His Ser Phe Cys Ala Phe Lys Ala Asp Asp Gly Pro Cys Lys Ala Ile Met Lys Arg Phe Phe Thr Arg

361  CGA CAG TGC GAA GAA TTT ATA TAT GGG GGA TGT GAA AAT CAG AAT CTG GAA GAG TGC AAA AAA ATG TGT ACA GGT          106
     Arg Gln Cys Glu Glu Phe Ile Tyr Gly Gly Cys Glu Phe Asn Arg Phe Glu Glu Cys Lys Lys Met Cys Thr Arg

451  GAT AAT GCA AAC ACG ATT ATA AAG ACA TTG CAA GAA AAG CCA GAT TTC TGC GAA GAT CCT GGA ATA TGT CGA GGT                 136
     Asp Asn Ala Asn Thr Ile Ile Lys Thr Leu Gln Glu Lys Pro Asp Phe Cys Glu Asp Pro Gly Ile Cys Arg Gly

541  TAT ATT ACC AGG TAT TTT TAT AAC AAT CAG AAA ACA CAG TGT GAA CGT TTC AAG TAT GGT GGA TGC CTG GGC AAT ATG AAC AAC TTT GAG  166
     Tyr Ile Thr Arg Tyr Phe Tyr Asn Asn Gln Lys Thr Gln Cys Glu Arg Phe Lys Tyr Gly Gly Cys Leu Gly Asn Met Asn Asn Phe Glu

631  ACA CTG GAA GAA TGC AAG AAC ATT TGT GAA GAT GGT CCC AAT TAT GGA ACC CAG CTC AAT GCT GTG AAT AAC         196
     Thr Leu Glu Glu Cys Lys Asn Ile Cys Glu Asp Gly Pro Asn Tyr Gly Thr Gln Leu Asn Ala Val Asn Asn

721  TCC CTG ACT CCG CAA TCA CAA AGC AAG GTT CCC AGC CTT TTT CAC GGT TGT CCC ACT CCA GCA GAC AGA GGA TTG TGT          226
     Ser Leu Thr Pro Gln Ser Gln Ser Lys Val Pro Ser Leu Phe His Gly Cys Pro Thr Pro Ala Asp Arg Gly Leu Cys

811  CGT GCC AAT GAG AAC AGA TTC TAC TAC AAT TCA GTC ATT GGG AAA TGC CGC CCA TTT AAG TAC AGT GGA TGT GGG AAT GAA AAC AAT     256
     Arg Ala Asn Glu Asn Arg Phe Tyr Tyr Asn Ser Val Ile Gly Lys Cys Arg Pro Phe Lys Tyr Ser Gly Cys Gly Asn Glu Asn Asn
```

FIG.3A

FIG.3B

901  TTT ACT TCC AAA CAA GAA TGT CTG AGG GCA TGT AAA AAA GGT TTC ATC CAA AGA ATA TCA AAA GGA GGC CTA ATT AAA ACC AAA AGA AAA
     Phe Thr Ser Lys Gln Glu Cys Leu Arg Ala Cys Lys Lys Gly Phe Ile Gln Arg Ile Ser Lys Gly Gly Leu Ile Lys Thr Lys Arg Lys 286

991  AGA AAG CAG AGA GTC AAA ATA GCA TAT GAA GAA ATT TTT GTT AAA AAT ATG TGA ATT TGT TAT AGC AAT GTA ACA TTA ATT CTA CTA    304
     Arg Lys Gln Arg Val Lys Ile Ala Tyr Glu Glu Ile Phe Val Lys Asn Met End

1081 AAT ATT TTA TAT GAA ATG TTT CAC TAT GAT CTA TTT CTC TTC TAA AAT CGT TTT AAT TAA TAT GTT CAT TAA ATT TTC TAT GCT TAT

1171 TGT ACT TGT TAT CAA CAC GTT TGT ATC AGA GTT GCT TTT CTA ATC TTG TTA AAT TGC TTA TTC TAG GTC TGT AAT TTA ACT GGC TAC

1261 TGG GAA ATT ACT TAT TTT CTG GAT CTA TCT GTA TTT TCA TTT AAC TAC AAA TTA TCA TAC TAC CGG CTA CAT CAA ATC AGT CCT TTG ATT

1351 CCA TTT GGT GAC CAT CTG TTT GAG AAT ATG ATC ATG TAA ATG ATT ATC TCC TTT ATA GCC TGT AAC CAG ATT AAG CCC CCC

```
     1                                                                                    50
1    PSLFNRDPPI PAAQRPDFCL EPPYTGPCKA RIIRYFYNAK AGLCQTFVYG GCRAKRNNFK SAEDCMRTCG GAIGPWGKTG GRAEGEGKG
2               FQTPPDLCQ  LPQARGPCKA ALLRYFYBST SNACEPFTYG GCCQSNNBNFE TTEMCLRICE PPQQTDKS
3               TERPDFCL   EPPYTGPCKA AMIRYFYNAK AGFCETFVYC GCRAKSNNFK SAEDCMRTCG GA
4               QGRPSFCN   LPAETGPCKA SFRQYYNSK  SGGCQQFIYG GCRGNQNRFD TTQQCGVCV
5               QCDKRDICR  LPPEQGPCKG RIPRYFYNPA SRMCESFIYG GCKGNKNNFK TKAECVRACR PPERPGVCPK TSGPGICLHG
6               QDHPKFCY   LPADPGRCKA HIPRFYYDSA SNKCNKFIYG GCPCNANNFK TWDECRQTCG ASA
7    RPDFCE     LPAETGLCKA YIRSFHYNLA AQQCLQFIYG  GCGGNANRFK TIDECRRTCV G
8    RPRFCE     LPAETGLCKA RIRSFHYNRA AQCQCLEFIYG GCGNANRFK  TIDECHRTCV G
9    HDRPTFCN   LAPESGRCRG HLRRIYYNLE SNKCKVFFYG  GCCGNANNFE TRDECRETCG GK
10   RDRPKFCY   LPADPGRCLA YMPRFYYNPA SNKCEKFIYG  GCRGNANNFK TWDECRHTCV ASGIQPR
11   QPRRKLCI   LHRNPGRCYD KIPAFYYNQK KKQCERFDWS  CCGGNSNRFK TIEECRRTCI G
12   RPYACE     LIVAAGPCMF FISAFYYSKG ANKCYPFTYS  GCRGNANRFV TIEKCRHACV V
13   LQHRTFCK   LPAEPGPCKA SIPAFYYMWA AKKCQLFHYG  GCCKCNANRFS TIEKCRHACV G
14   QPLRKLCI   LHRNPGRCYQ KIPAFYYNQK KIPSFYYKMK  GCCGGNSNRFK TIEECRRTCI RK
15   AAKYCK     LPLRIGPCKR KIPSFYYKMK AKQCQLPFDYS  GCCGGNANRFK TIEECRRTCV G
16   RQRHRDCD   KPPDKGNC.G PVRAFYYDTR LKTCKAFQYR  GCDCDHGNFK SDHLCRCECE LY
17   RQRHRDCD   KPPDKGNC.G PVRAFYYDTR LKTCKAFQYR  GCDCDHGNFK TETLCRCECL VYP
18   RKRHPDCD   KPPDIKIC.Q TVRAFYYKPS AKRCVQFRYG  GCDCDHGNFK SDHLCRCECE LYR
19(1) KEDSCQ    LDHAQGPCLG MISRYFYNGT SWACETFQYG  GCLGNGNNFA SQKECLQTCR T
19(2)  VAACN    LPIVQGPCRA FIRLWAFDAA QGKCVLFTYG  GCRGNGNKFY SQKECKEYCG IPGDGDEELL R
20(1)  KEDSCQ   LGYSQGPCLG MIKRYFYNGS SWACETFHYG  GCMGNGNNFV SQKECLQTCR T
20(2)  VSACS    LPIVQGPCRA FIRLWAFDAA QGKCVLFNYG  GCCKCVLFNYG SQKECKEYCG VPGEEDEELL R
21(1)  KADSCQ   LDYSQGPCLG LFKRYFYNGT SWACETFLYG  GCMCNLNNFL SQKECLQTCR T
21(2)  VEACN    LPIVQGPCRA FIQLWAFDAV KGKCVRFSYG  GCKGNGNKFY SQKECKEYCG IPGEADERLL R
22(1)  KEDSCQ   LGYSAGPCMG MTSRYFYNGT SWACETFQYG  GCMCNGNNFV TEKECLQTCR T
22(2)  VAACN    LPIVRGPCRA FIQLWAFDAV KGKCVLFPYG  GCCGNGNKFY SEKECREYCG VPGDGDEELL RFSN
23(1)  LKLMHSFCA FKADDGPCKA IMKRFFFNIF TRQCEEFIYG  GCEGNQNRFE SLEECKKMCT RDNANRIIKT TL
23(2)  QQEKPDFCF LEEDPGICRG YITRYFYNNQ TKQCERFKYG  GCLGMWNNFE TLEECKNICE DGPNGFQVDN YG
23(3)  EFHGPSWCL TPADRGLCRA NENRFYYNSV IGKCRPFKYS  GCCGNENNFT SKQECLRACK KGFIQRISKG GL

Consensus    ........C  .....G.C.. ..........  ..C.F.... GC.......  .....F......  ..C..C.  ..C...
```

FIG. 6

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 1431 base pairs
      (B) TYPE: nucleic acid
      (C) STRANDEDNESS: single
      (D) TOPOLOGY: linear (ii) MOLECULE TYPE: cDNA (vi) ORIGINAL SOURCE:
      (F) TISSUE TYPE: Human placenta (vii) IMMEDIATE SOURCE:
      (A) LIBRARY: Human placental-derived lambda-P9 clone
      (B) CLONE: Tissue factor inhibitor (TFI) cDNA (ix) FEATURE:
      (A) NAME/KEY: 5'UTR
      (B) LOCATION: 1...132
      (D) OTHER INFORMATION: *tag=a
      (A) NAME/KEY: 3'UTR
      (B) LOCATION: 1045...1431
      (D) OTHER INFORMATION: *tag=b
      (A) NAME/KEY: CDS
      (B) LOCATION: 3...104
      (D) OTHER INFORMATION: *tag=c (x) PUBLICATION INFORMATION:
      (H) DOCUMENT NUMBER: EP 318451
      (I) FILING DATE: 22-JUL-1988
      (J) PUBLICATION DATE: 31-MAY-1988
      (K) RELEVANT RESIDUES IN SEQ ID NO:

(xi) SEQUENCE DESCRIPTION: SEQ ID NO:1:

```
GGCGGGTCTG CTTCTAAAAG AAGAAGTAGA GAAGATAAAT CCTGTCTTCA ATACCTGGAA      60

GGAAAAACAA AATAACCTCA ACTCCGTTTT GAAAAAAACA TTCCAAGAAC TTTCATCAGA     120

GATTTTACTT AGATGATTTA CACAATGAAG AAAGTACATG CACTTTGGGC TTCTGTATGC     180

CTGCTGCTTA ATCTTGCCCC TGCCCCTCTT AATGCTGATT CTGAGGAAGA TGAAGAACAC     240

ACAATTATCA CAGATACGGA GTTGCCACCA CTGAAACTTA TGCATTCATT TTGTGCATTC     300

AAGGCGGATG ATGGCCCATG TAAAGCAATC ATGAAAAGAT TTTTCTTCAA TATTTTCACT     360

CGACAGTGCG AAGAATTTAT ATATGGGGCA TGTGAAGGAA ATCAGAATCG ATTTGAAAGT     420

CTGGAAGAGT GCAAAAAAAT GTGTACAAGA GATAATGCAA ACAGGATTAT AAAGACAACA     480

TTGCAACAAG AAAAGCCAGA TTTCTGCTTT TTGGAAGAAG ATCCTGGAAT ATGTCGAGGT     540

TATATTACCA GGTATTTTTA TAACAATCAG ACAAAACAGT GTGAACGTTT CAAGTATGGT     600

GGATGCCTGG GCAATATGAA CAATTTTGAG ACACTGGAAG AATGCAAGAA CATTTGTGAA     660
```

```
GATGGTCCGA ATGGTTTCCA GGTGGATAAT TATGGAACCC AGCTCAATGC TGTGAATAAC      720

TCCCTGACTC CGCAATCAAC CAAGGTTCCC AGCCTTTTTG AATTTCACGG TCCCTCATGG      780

TGTCTCACTC CAGCAGACAG AGGATTGTGT CGTGCCAATG AGAACAGATT CTACTACAAT      840

TCAGTCATTG GGAAATGCCG CCCATTTAAG TACAGTGGAT GTGGGGGAAA TGAAAACAAT      900

TTTACTTCCA AACAAGAATG TCTGAGGGCA TGTAAAAAAG GTTTCATCCA AAGAATATCA      960

AAAGGAGGCC TAATTAAAAC CAAAAGAAAA AGAAAGAAGC AGAGAGTGAA AATAGCATAT     1020

GAAGAAATTT TTGTTAAAAA TATGTGAATT TGTTATAGCA ATGTAACATT AATTCTACTA     1080

AATATTTTAT ATGAAATGTT TCACTATGAT TTTCTATTTT TCTTCTAAAA TCGTTTTAAT     1140

TAATATGTTC ATTAAATTTT CTATGCTTAT TGTACTTGTT ATCAACACGT TTGTATCAGA     1200

GTTGCTTTTC TAATCTTGTT AAATTGCTTA TTCTAGGTCT GTAATTTATT AACTGGCTAC     1260

TGGGAAATTA CTTATTTTCT GGATCTATCT GTATTTTCAT TTAACTACAA ATTATCATAC     1320

TACCGGCTAC ATCAAATCAG TCCTTTGATT CCATTTGGTG ACCATCTGTT TGAGAATATG     1380

ATCATGTAAA TGATTATCTC CTTTATAGCC TGTAACCAGA TTAAGCCCCC C             1431

(2) INFORMATION FOR SEQ ID NO:2:

(i) SEQUENCE CHARACTERISTICS:
        (A) LENGTH: 304 amino acids
        (B) TYPE: amino acid
        (C) STRANDEDNESS: single
        (D) TOPOLOGY: linear (ii) MOLECULE TYPE: protein (vii) IMMEDIATE SOURCE:
        (B) CLONE: A.A. seq. of human tissue factor inhibitor (TFI)

(ix) FEATURE:
        (A) NAME/KEY: Signal Sequence
        (B) LOCATION: 1...28
        (D) OTHER INFORMATION: Signal region
        (A) NAME/KEY: mat_peptide
        (B) LOCATION: 29...304
        (D) OTHER INFORMATION:

(xi) SEQUENCE DESCRIPTION: SEQ ID NO:2:

Met Ile Tyr Thr Met Lys Lys Val His Ala Leu Trp Ala Ser Val Cys
            -25                 -20                 -15

Leu Leu Leu Asn Leu Ala Pro Ala Pro Leu Asn Ala Asp Ser Glu Glu
        -10                  -5                   1

Asp Glu Glu His Thr Ile Ile Thr Asp Thr Glu Leu Pro Pro Leu Lys
 5               10                  15                  20

Leu Met His Ser Phe Cys Ala Phe Lys Ala Asp Asp Gly Pro Cys Lys
                 25                  30                  35

Ala Ile Met Lys Arg Phe Phe Phe Asn Ile Phe Thr Arg Gln Cys Glu
             40                  45                  50

Glu Phe Ile Tyr Gly Ala Cys Glu Gly Asn Gln Asn Arg Phe Glu Ser
         55                  60                  65

Leu Glu Glu Cys Lys Lys Met Cys Thr Arg Asp Asn Ala Asn Arg Ile
     70                  75                  80

Ile Lys Thr Thr Leu Gln Gln Glu Lys Pro Asp Phe Cys Phe Leu Glu
 85                  90                  95                 100

Glu Asp Pro Gly Ile Cys Arg Gly Tyr Ile Thr Arg Tyr Phe Tyr Asn
                105                 110                 115

Asn Gln Thr Lys Gln Cys Glu Arg Phe Lys Tyr Gly Gly Cys Leu Gly
```

```
                    120                 125                 130
Asn Met Asn Asn Phe Glu Thr Leu Glu Glu Cys Lys Asn Ile Cys Glu
        135                 140                 145

Asp Gly Pro Asn Gly Phe Gln Val Asp Asn Tyr Gly Thr Gln Leu Asn
        150                 155                 160

Ala Val Asn Asn Ser Leu Thr Pro Gln Ser Thr Lys Val Pro Ser Leu
165                 170                 175                 180

Phe Glu Phe His Gly Pro Ser Trp Cys Leu Thr Pro Ala Asp Arg Gly
                185                 190                 195

Leu Cys Arg Ala Asn Glu Asn Arg Phe Tyr Tyr Asn Ser Val Ile Gly
            200                 205                 210

Lys Cys Arg Pro Phe Lys Tyr Ser Gly Cys Gly Gly Asn Glu Asn Asn
            215                 220                 225

Phe Thr Ser Lys Gln Glu Cys Leu Arg Ala Cys Lys Lys Gly Phe Ile
        230                 235                 240

Gln Arg Ile Ser Lys Gly Gly Leu Ile Lys Thr Lys Arg Lys Arg Lys
245                 250                 255                 260

Lys Gln Arg Val Lys Ile Ala Tyr Glu Glu Ile Phe Val Lys Asn Met
                265                 270                 275
```

ANTIBODIES TO TISSUE FACTOR INHIBITOR

CROSS-REFERENCE TO RELATED APPLICATION

This application is a continuation of 08/463,323 filed Jun. 5, 1995 now U.S. Pat No. 5,849,875 which is a continuation of 08/355,351 filed Dec. 13, 1994, abandoned, which is a continuation of 07/566,280 filed Aug. 13, 1990, abandoned, which is a divisional of 07/123,753 filed Nov. 23, 1987, now U.S. Pat. No. 4,966,852, which is a continuation-in-part of 07/077,366, filed Jul. 23, 1987 now abandoned.

BACKGROUND OF THE INVENTION

This invention relates to a coagulation inhibitor known as tissue factor inhibitor (TFI) and alternatively as lipoprotein associated coagulation inhibitor (LACI). More particularly, the invention relates to a CDNA clone representing essentially the full size TFI.

The coagulation cascade that occurs in mammalian blood comprises two distinct systems—the so-called intrinsic and extrinsic systems. The latter system is activated by exposure of blood to tissue thromboplastin (Factor III), hereinafter referred to as tissue factor (TF). Tissue factor is a lipoprotein that arises in the plasma membrane of many cell types and in which the brain and lung are particularly rich. Upon coming into contact with TF, plasma Factor VII or its activated form, Factor $VII_a$, forms a calcium-dependent complex with TF and then proteolytically activates Factor X to Factor $X_a$, and Factor IX to Factor $IX_a$.

Early studies concerning the regulation of TF-initiated coagulation showed that incubation of TF (in crude tissue thromboplastin preparations) with serum inhibited its activity in vitro and prevented its lethal effect when it was infused into mice. Extensive studies by Hjort, *Scand. J. Clin. Lab. Invest.* 9, Suppl. 27, 76–97 (1957), confirmed and extended previous work in the area, and led to the conclusion that an inhibitory moiety in serum recognized the Factor VII-TF complex. Consistent with this hypothesis are the facts that the inhibition of TF that occurs in plasma requires the presence of $Ca^{2+}$ (which is also necessary for the binding of Factor $VII/VII_a$ to TF) and that inhibition can be prevented and/or reversed by chelation of divalent cations with EDTA. More recent investigations have shown that not only Factor $VII_a$ but also catalytically active Factor $X_a$ and an additional factor are required for the generation of TF inhibition in plasma or serum. See Broze and Miletich, *Blood* 69, 150–155 (1987), and Sanders et al., *Ibid.*, 66, 204–212 (1985). This additional factor, defined herein as tissue factor inhibitor (TFI), and alternatively as lipoprotein associated coagulation inhibitor (LACI), is present in barium-absorbed plasma and appears to be associated with lipoproteins, since TFI functional activity segregates with the lipoprotein fraction that floats when serum is centrifuged at a density of 1.21 g/cm³. According to Broze and Miletich, supra, and *Proc. Natl. Acad. Sci. USA* 84, 1886–1890 (1987), HepG2 cells (a human hepatoma cell line) secrete an inhibitory moiety with the same characteristics as the TFI present in plasma.

In copending application Ser. No. 07/077,366, filed Jul. 23, 1987 now abandoned, a purified tissue factor inhibitor (TFI) is disclosed which was secreted from HepG2 cells. It was found to exist in two forms, a $TFI_1$, migrating at about 37–40,000 daltons and a $TFI_2$ at about 25–26,000 daltons, as determined by sodium dodecylsulfate polyacrylamide gel electrophoresis (SDS-PAGE). A partial N-terminal amino acid sequence for the TFI was assigned as:

```
 1
X-X-Glu-Glu-Asp-Glu-Glu-His-Thr-Ile-Ile-Thr-Asp-
    15 16
Thr-Glu-Leu-Pro-Pro-Leu-Lys-Leu-Met-His-Ser-Phe-
     27
(Phe)-Ala
``` wherein X—X had not been determined. The disclosure of said application is incorporated herein by reference.

BRIEF DESCRIPTION OF THE INVENTION

In accordance with the present invention, the complete coding sequence of a cDNA clone representing essentially the full size tissue factor inhibitor (TFI) has been developed.

Initially, human placental and fetal liver λgt11 cDNA libraries were screened with a rabbit polyclonal antiserum raised against a purified TFI. Immunologically positive clones were further screened for $^{125}$I-Factor $X_a$ binding activity. Seven clones were obtained which were immunologically and functionally active. The longest clone, placental-derived λP9, was 1.4 kilobases (kb) long while the other six were 1.0 kb in length. Partial DNA sequencing showed the 1.0 kb clones to have sequences identical to part of the longer 1.4 kb clone. Nucleotide sequence analysis showed that λP9 consisted of a 1432 basepair (bp) cDNA insert that includes a 5'-noncoding region of 133 bp, an open reading frame of 912 bp, a stop codon, and a 3'-noncoding region of 384 bp.

The cDNA sequence encodes a 31,950 Dalton protein of 276 amino acids which includes 18 cysteines and 7 methionines. The translated amino acid sequence shows that a signal peptide of about 28 amino acids precedes the mature TFI protein. It will be understood that the "mature" TFI is defined to include both TFI and methionyl TFI by virtue of the ATG translational codon in the λP9 clone described herein.

There are three potential N-linked glycosylation sites in the TFI protein with the sequence Asn-X-Ser/Thr, wherein X can be any of the common 20 amino acids. These sites are at amino acid positions Asn 145, Asn 195, and Asn 256, when the first methionine after the 5'-noncoding region is assigned amino acid position +1.

The translated amino acid sequence of TFI shows several discernible domains, including a highly negatively charged N-terminal, a highly positively charged carboxy-terminal, and an intervening portion consisting of 3 homologous domains with sequences typical of Kunitz-type enzyme inhibitors. Based on a homology study, TFI appears to be a member of the basic protease inhibitor gene superfamily.

The original source of the protein material for developing the cDNA clone λP9 was human placental tissue. Such tissue is widely available after delivery by conventional surgical procedures. The λgt11 (lac5 nin5 c1857 S100) used herein is a well-known and commonly available lambda phage expression vector. Its construction and restriction endonuclease map is described by Young and Davis, *Proc. Natl. Acad. Sci. USA* 80, 1194–1198 (1983).

Northern blot analysis showed that the following liver-derived cell lines: Change liver, HepG2 hepatoma, and SK-HEP-1 hepatoma, all contained 2 major species of mRNA (1.4 and 4.4 kb) which hybridized with the TFI cDNA.

The cloning of the cDNA for TFI and development of its entire protein sequence and structural domains as disclosed herein permits detailed structure-functional analyses and provides a foundation for study of its biosynthetic regulations. The invention thus is important to medical science in the study of the coagulation cascade with respect to agents which are able to inhibit Factor $X_a$ and Factor $VII_a$/TF enzymatic complex.

DETAILED DESCRIPTION OF THE INVENTION

While the specification concludes with claims particularly pointing out and distinctly claiming the subject matter regarded as forming the present invention, it is believed that the invention will be better understood from the following detailed description of preferred embodiments of the invention taken in conjunction with the appended drawings, in which:

FIG. 1 shows the screening of λgt11 clones with $^{125}$I-Factor $X_a$. Cloned phage lysates (0.1 ml) were spotted on a nitrocellulose paper by suction using a dot blot apparatus. The nitrocellulose paper was the n probed with $^{125}$I-Factor $X_a$ and autoradiographed as described hereinafter. The clones that appear as dark spots are positive clones that bind $^{125}$I-Factor $X_a$. Control λgt11 (lower right corner) and other clones do not bind $^{125}$I-Factor $X_a$.

Figure 2:
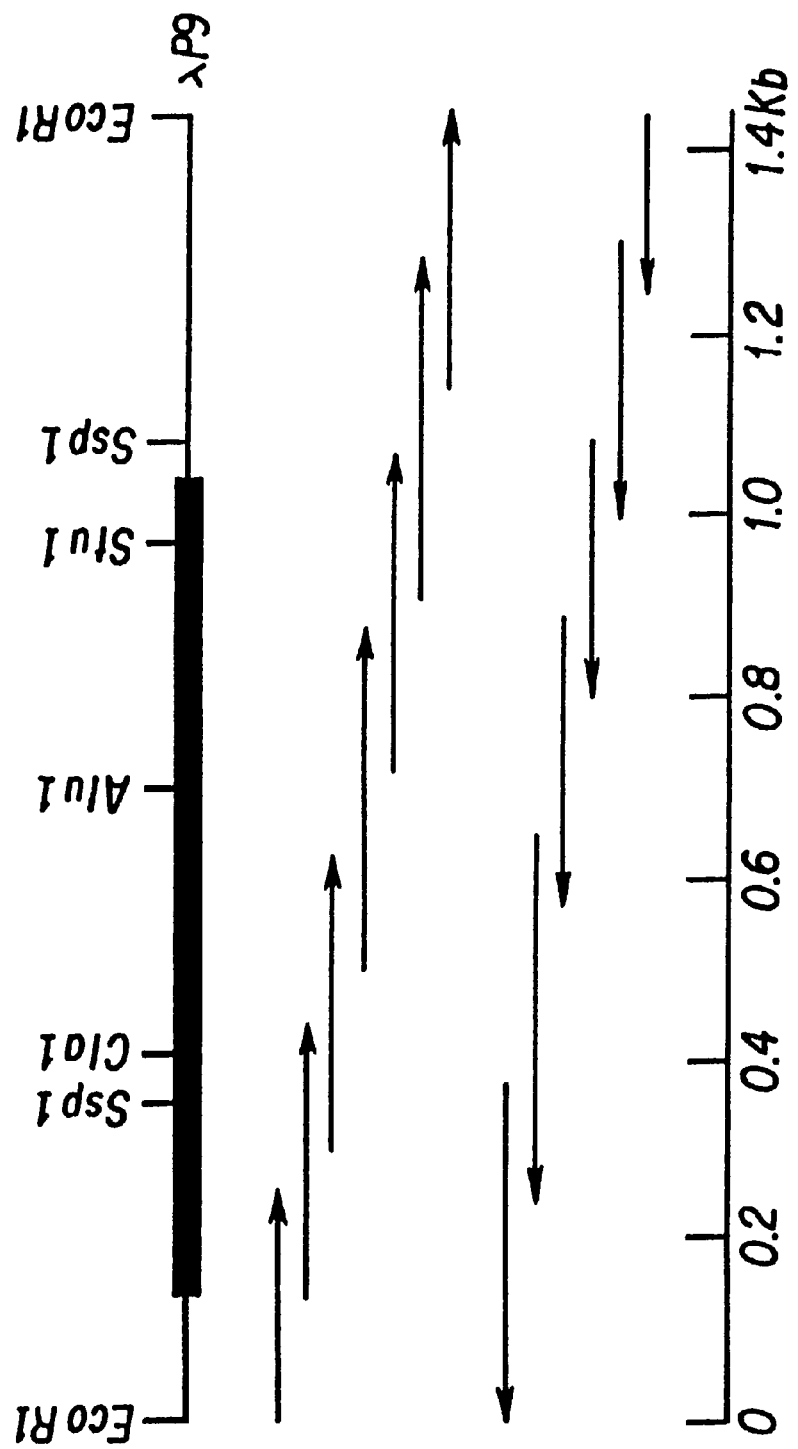

FIG. 2 shows a partial restriction map and sequencing strategy for the λP9 inserts. The scale at the bottom indicates the nucleotide position. The thick bar represents the coding region. The thin bars represent 5'- and 3'-noncoding regions. The restriction endonuclease sites were confirmed by digestion. The arrows show the overlapping M13 clones used to sequence the cDNA.

FIG. 3 shows the nucleotide sequence and translated amino acid sequence of the human TFI cDNA. Nucleotides are numbered on the left and amino acids on the right. The underlined sequences have been independently confirmed by amino acid sequence analysis of the purified TFI protein and two $V_8$ protease+trying digested peptides. Amino acid+1 was assigned to the first methionine after a stop codon of the 5'-noncoding region. Potential N-lined glycosylation sites are marked by asterisks.

Figure 4:
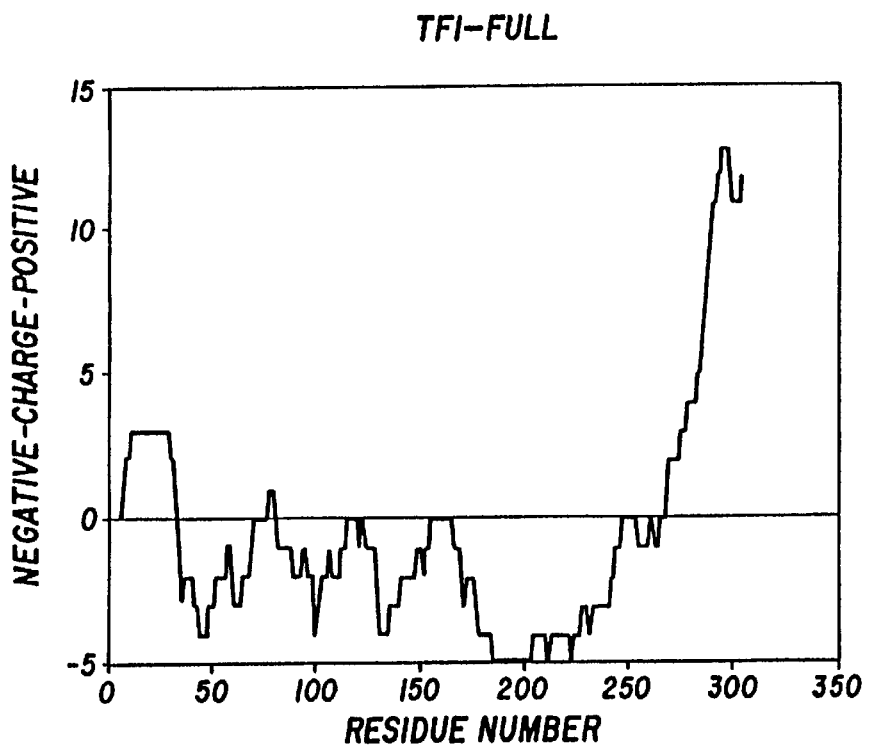

FIG. 4 is a graphical representation which shows the charge distribution of the amino acid sequence in TFI. Charges are calculated from the first residue to the i-th residues and displayed at the i-th residue. Thus the value of the i-th position is the summation of all charges from the first residue to the i-th residue and the difference of the charges between the i-th and j-th residue (j>i) is the net charge of the fragment from i-th to j-th residue.

Figure 5:
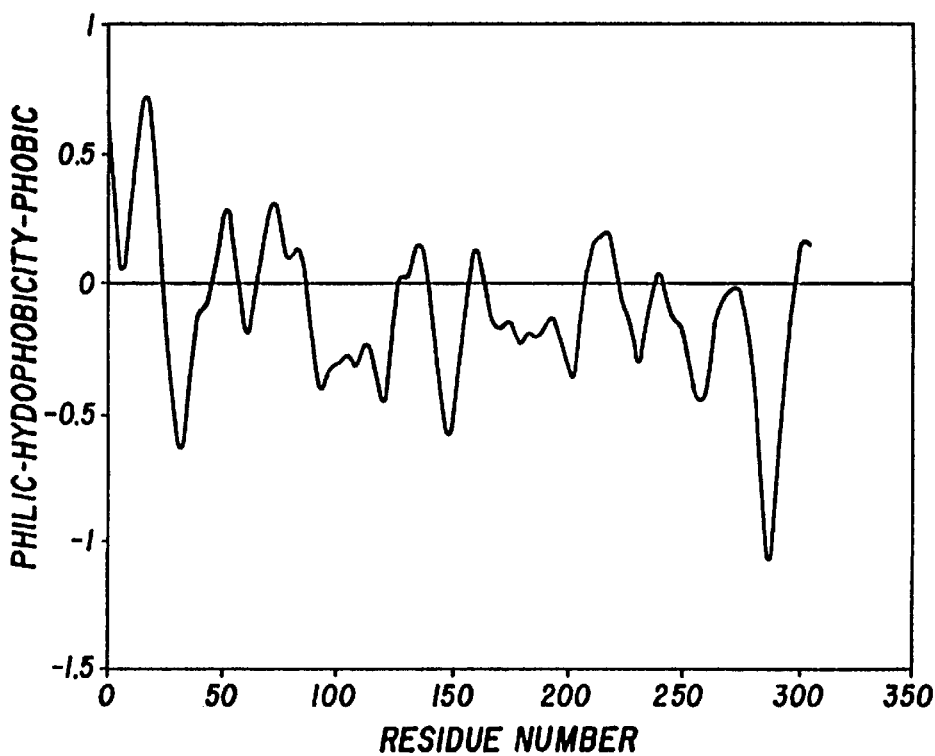

FIG. 5 is a graphical representation which shows the hydrophobicity profile of TFI. The hydrophobicity profile was analyzed by a computer program whereby the hydrophobicity index of the amino acid residues is defined as the depth to which an amino acid residue is buried inside a protein (from X-ray crystallographic data) [Kidera et al., *J. Protein Chem.* 4, 23–55 (1985)]. The hydrophobicity profile along the sequence was smoothed using the program ICSSCU in IMSL Library [IMSL Library Reference Manual, 9th ed., Institute for Mathematical and Statistical Subroutine Library, Houston, Texas (1982)].

FIG. 6 shows an alignment of the basic protease inhibitor domains of TFI with other basic protease inhibitors. All the sequences except TFI were obtained from the National Biomedical Research Foundation Protein Sequence Database (Georgetown University, Washington, D.C., release Jun. 13, 1987). 1. Bovine basic protease inhibitor precursor; 2. Bovine colostrum trypsin inhibitor; 3. Bovine serum basic protease inhibitor; 4. Edible snail isoinhibitor K; 5. Red sea turtle basic protease inhibitor (only amino acids 1–79 presented); 6. Western sand viper venom basic protease inhibitor I; 7. Ringhals venom basic protease inhibitor II; 8. Cape cobra venom basic protease inhibitor II; 9. Russell's viper venom basic protease inhibitor II; 10. Sand viper venom basic protease inhibitor III; 11. Eastern green mamba venom basic protease inhibitor I homolog; 12. Black mamba venom basic protease inhibitor B; 13. Black mamba venom basic protease inhibitor E; 14. Black mamba venom basic protease inhibitor I; 15. Black mamba venom basic protease inhibitor K; 16. β-1-Bungarotoxin B chain (minor); 17. β-1-Bungarotoxin B chain (major); 18. β-2-Bungarotoxin B chain; 19. Horse inter-α-trypsin inhibitor [amino acids 1–57 (1); 58–123 (2)]; 20. Pig inter-α-trypsin inhibitor [amino acids 1–57(1); 58–123(2)]; 21. Bovine inter-α-trypsin inhibitor [amino acids 1–57(1); 58–123(2)]; 22. Human α-1-miroglobulin/inter-α-trypsin inhibitor precursor [amino acids 227–283(1); 284–352(2)]; 23. TFI [amino acids 47–117(1); 118–188(2); 210–280(3)]. Gaps were included in 16, 17, 18 to achieve best alignment. Standard one letter codes for amino acids are used.

Figure 7:
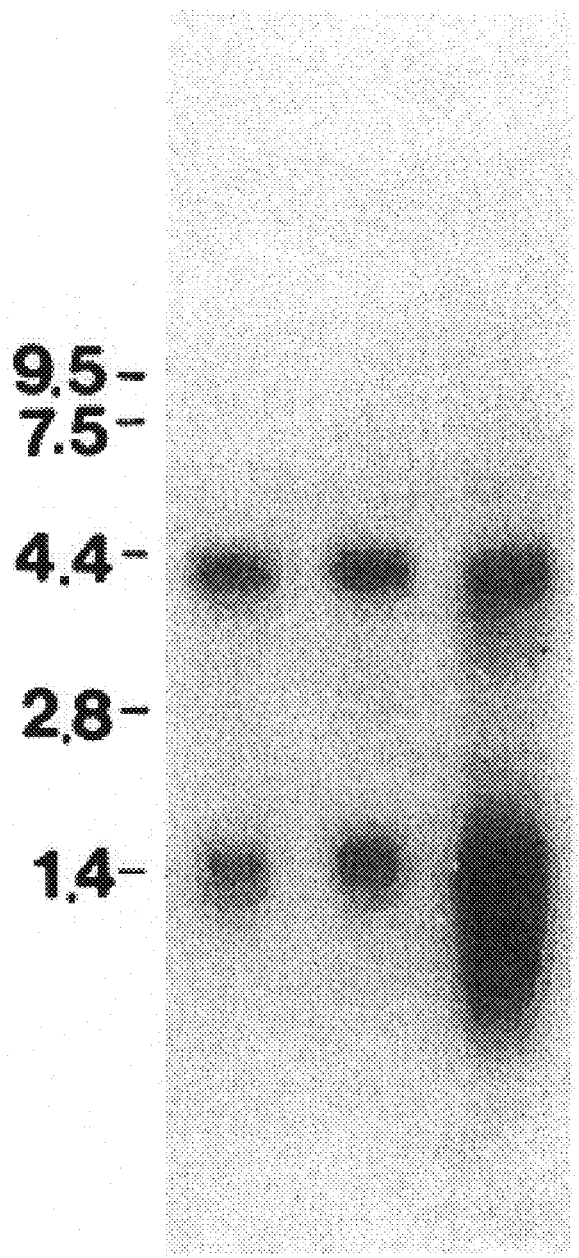

FIG. 7 shows the Northern blot analysis of RNAs from 3 liver-derived cell lines. Ten μg of poly(A)$^+$RNA were used per lane. Lane 1, Chang liver cell; lane 2, SK-HEP-1 hepatoma cell; lane 3, HepG2 hepatoma cell.

Standard biochemical nomenclature is used herein in which the nucleotide bases are designated as adenine (A); thymine (T); guanine (G); and cytosine (C). Corresponding nucleotides are, for example, deoxyguanosine-5'-triphosphate (dGTP). As is conventional for convenience in the structural representation of a DNA nucleotide sequence, only one strand is shown in which A on one strand connotes T on its complement and G connotes C. Amino acids are shown either by three letter or one letter abbreviations as follows:

| Abbreviated Designation | | Amino Acid |
| --- | --- | --- |
| A | Ala | Alanine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

Commonly available restriction endonucleases described herein have the following restriction sequences and (indicated by arrows) cleavage patterns:

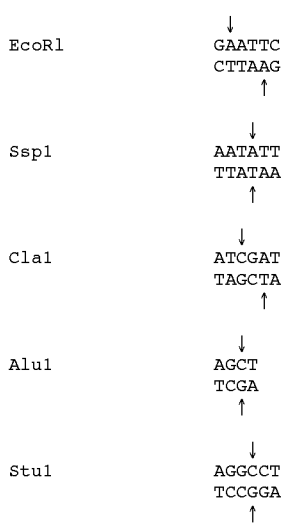

In order to illustrate specific preferred embodiments of the invention in greater detail, the following exemplary laboratory preparative work was carried out.

EXAMPLE 1

Materials

Human placental and fetal liver cDNA libraries were obtained from Clonetech. The protoblot immunoscreening kit was purchased from Promega Biotech. Restriction enzymes were from New England Biolabs. Calf intestine alkaline phosphatase, T4 DNA ligase, DNA polymerase I (Klenow), exo-nuclease III and S1 nuclease were from Boehringer Mannheim. dNTPs were from P. L. Biochemicals. 5'-[$\alpha$-$^{35}$S]-thio-dATP (600 Ci/mmol) was from Amersham. Sequencing kit (Sequenase) was from United States Biochemicals. Chang liver cells (ATCC CCL 13) and HepG2 hepatoma cells (ATCC HB 8065) were obtained from the American Type Culture Collection. SK-HEP-1 hepatoma cells were originally derived from a liver adenocarcinoma by G. Trempe of Sloan-Kettering Institute for Cancer Research in 1971 and are now widely and readily available.

$^{125}$I-Factor $X_a$ was prepared by radio-labeling using Iodogen. The specific activity was 2000 dpm/ng. Greater than 97% of radioactivity was precipitable with 10% trichloroacetic acid (TCA). The iodinated protein retained <80% of their catalytic activity toward Spectrozyme $X_a$ (American Diagnostica product).

An anti-TFI-Ig Sepharose® 4B column was prepared as follows: A peptide called TFI-peptide) containing a sequence corresponding to the amino acid sequence 3–25 of the mature TFI was synthesized using Biosystem's solid phase peptide synthesis system. The TFI-peptide (5 mg) was conjugated to 10 mg of Keyhole lympet hemocyanin by glutaraldehyde. Two New Zealand white rabbits were each immunized by intradermal injection with a homogenate containing 1 ml of Freund complete adjuvant and 1 ml of conjugate (200 µg of TFI-peptide). One month later the rabbits were each boosted with a homogenate containing 1 ml of Freund incomplete adjuvant and 1 ml of conjugate (100 µg of conjugate). Antiserum was collected each week for 3 months and booster injections were performed monthly. To isolate specific antibody against TFI-peptide, the antiserum was chromatographed on a TFI-peptide Sepharose 4B column. The column was washed with 10 volumes of PBS (0.4 M NaCl-0.1 M benzamidine-1% Triton® X-100) and the same solution without Triton X-100. The antibody was eluted with 0.1 M glycine/HCl, pH 2.2, immediately neutralized by adding 1/10 volume of 1 M Tris-OH and dialyzed against saline solution. The isolated antibody was coupled to cyanogen bromide activated Sepharose 4B by the manufacturer's (Pharmacia) method and used to isolate TFI from the cell culture medium.

Chang liver cell was cultured by the method described previously by Broze and Miletich, *Proc. Natl. Acad. Sci. USA* 84, 1886–1890 (1987). The conditioned medium was chromatographed on the anti-TFI-Ig Sepharose 4B column. The column was washed with 10 volumes of PBS-1% Triton X-100 and PBS. The bound TFI was eluted with 0.1 M glycine/HCl, pH 2.2. The immunoaffinity isolated TFI was further purified by preparative sodium dodecylsulfate polyacrylamide gel electrophoresis (Savant apparatus). Amino acid analysis of the final product showed the same amino terminal sequence as the TFI isolated from HepG2 cells as described in copending application, Ser. No. 77,366, filed Jul. 23, 1987. The isolated Chang liver TFI was then used to immunize rabbits by the immunization protocol described above. The antiserum obtained had a titer of about 100 µg/ml in the double immunodiffusion test. This antiserum was used in the immuno-screening of λgtll cDNA libraries.

Methods

Isolation of cDNA clones. Methods for screening the placental and fetal liver cDNA libraries with antibody, plaque purification, and preparation of λ-phage lysate and DNA were as described by Wun and Kretzmer, *FEBS Lett.* 1, 11–16 (1987). The antiserum was pre-adsorbed with BNN97 λgtll lysate and diluted 1/500 for screening the library.

Screening of factor $X_a$ binding activity. Recombinant proteins induced by isopropyl-β-thiogalactoside from immuno-positive λ-phage isolates or from control λgtll were screened for Factor $X_a$ binding activity. The λ-phage lysates (0.1 ml) were filtered through a nitrocellulose paper using a dot-blot apparatus (Bio Rad). The nitrocellulose paper was then immersed and agitated in a phosphate buffered saline containing 5 mg/ml bovine serum albumin and 2.5 mg/ml bovine gamma globulin at room temperature for 1 h. The solution was replaced with $^{125}$I-Factor $X_a$ (1.0×10$^6$ cmp/ml) dissolved in the same solution supplemented with 0.1 mg/ml heparin and the agitation continued for another hour. The nitrocellulose paper was then washed with phosphate buffered saline containing 0.05% Tween® 20. The washing buffer was changed every 5 min., 4 times. The nitrocellulose paper was then air-dryed and prepared for autoradiography using Kodak XR5 film. The film was developed after 1 week exposure.

Preparation of poly(A)$^+$ RNA and Northern blotting. Total RNAs were prepared from cultured Chang liver cell, HepG2 hepatoma cell and SK-HEP-1 hepatoma cell using the sodium perchlorate extraction method of Lizardi, and Engelberg, *Anal. Biochem.* 98, 116–122, (1979). Poly(A)$^+$ RNAs were isolated by batch-wise adsorption on oligo(dT)-cellulose (P-L Biochemical, type 77F) using the procedure recommended by the manufacturer. For Northern blot analysis, 10 µg each of poly(A)$^+$ RNA was treated with glyoxal [Thomas, *Methods Enzymol.* 100, 255–266 (1983)] and subjected to agarose gel electrophoresis in a buffer containing 10 mM sodium phosphate, pH 7.0. Bethesda Research Laboratory's RNA ladder was used as a molecular weight marker. The RNAs were transblotted onto a nitrocellulose paper which was then baked at 80° for 2 h. The insert DNA of λP9 clone was radiolabeled with $^{32}$P by nick translation and used as a probe [Maniatis et al., *Molecular*

*Cloning: A Laboratory Model*, Cold Spring Laboratory, Cold Spring Harbor, N.Y., (1982)]. The blot was hybridized with $5 \times 10^6$ cpm of the probe in 5 ml of a solution containing 50% formamide, 5×SSC, 50 mM sodium phosphate, pH 7.0, 250 μg/ml denatured salmon sperm DNA, and 1× Denhardt's solution at 42° for 16 h. The filter was washed in 0.1% sodium dodecylsulfate (SDS), 2×SSC at room temperature 3 times, each time 5 min., and in 0.1% SDS, 0.2×SSC at 50° twice, each 5 min. The nitrocellulose paper was then air dried, autoradiographed for 3 days at −70° using Kodak XAR-5 film and intensifying screen.

Other recombinant DNA methods. Preparation of cloned λgt11 DNA, subcloning in pUC19 plasmid and M13mp18 vector, generation of deletion by exonuclease III digestion and DNA sequencing by dideoxy method [Sanger et al., *Proc. Natl. Acad. Sci. USA* 83, 6776–6780 (1977)], were performed as described by Wun and Kretzmer, supra.

The program FASTP written by Lipman and Pearson, *Science* 227 1435–1441 (1985), was used to identify homologous families of proteins from National Biomedical Research Foundation Sequence Data Bank (release Jun. 13, 1987) and to align the sequences within the homologous family.

RESULTS

Screening of cDNA Libraries

A number of cell lines were screened for the presence of TFI in the conditioned media and it was found that several liver-derived cell lines, Chang liver, HepG2 hepatoma, and SK-HEP-1 hepatoma secrete TFI in culture. Initially, an antiserum against TFI was used to screen a human fetal liver λgt11 cDNA library ($10^6$ plaque forming units), and 15 immunologically positive clones were obtained. Subsequently, the same method was used to screen a placental λgt11 cDNA library. Out of $10^6$ plaque forming units, 10 immunologically positive clones were obtained. These clones were plaque purified and the lysates of the purified clones were tested for the functional activity of TFI. The isopropylthio-galactoside induced phage lysates were absorbed on the nitrocellulose paper and screened for the $^{125}$I-Factor $X_a$ binding activity. FIG. 1 demonstrates that some of these immunologically positive clones showed the ability to bind the $^{125}$I-Factor $X_a$ on the nitrocellulose paper. In all, 3 out of 15 immunologically positive fetal liver clones, and 4 out of 10 immunologically positive placental clones showed $^{125}$I-Factor $X_a$ binding activity. These immunologically and functionally positive clones were digested with EcoR1 and the size of the inserts were estimated by gel electrophoresis. One clone from placental library (λP9) had an insert of approximately 1.4 kb, while all the other clones contain inserts of approximately 1.0 kb. Partial DNA sequencing has shown that 1.0 kb clones contain sequences identical to part of the longer 1.4 kb placental clone (λP9). The λP9 was therefore selected for complete sequencing.

Nucleotide Sequence and Predicted Protein Sequence of TFI cDNA Isolate

The λP9 clone was subjected to restriction mapping, M13 subcloning and sequencing by the strategy shown in FIG. 2. The entire sequence was determined on both strands by the exonuclease III deletion method [Henikoff, *Gene* 28, 351–359 (1984)] and found to consist of 1432 bases in length. The sequence is shown in FIG. 3. It contains a 5'-noncoding region of 133 bases, an open reading frame of 912 nucleotides, and a 3'-noncoding region of 387 nucleotides. The first ATG occurs at nucleotide 134 in the sequence TAGATGA which was closely followed by a second ATG at nucleotide 146 in the sequence ACAATGA. These are possibly the initiation sequences, although they differ from the proposed consensus sequence for initiation by eukaryotic ribosome, ACCATGG [Kozak, *Cell* 44, 283–292 (1986)]. Twenty-eight amino acids precede a sequence corresponding to the N-terminal of the mature protein. The length and composition of the hydrophobic segment of these 28 amino acids are typical of signal sequences [Von Heijne, *Eur. J. Biochem.* 133, 17–21 (1983); *J. Mol. Biol.* 184, 99–105 (1985)]. A signal peptidase possibly cleaves at $Ala_{28}$-$Asp_{29}$ to give rise to a mature protein. The sequence predicted for mature TFI consists of 276 amino acids that contains 18 cysteine residues and 7 methionines. The calculated mass of 31,950 Daltons based on the deduced protein sequence for mature TFI is somewhat lower than the 37–40 kDa estimated by sodium dodecyl sulfate polyacrylamide gel electrophoresis of isolated protein, and the difference probably reflects the contribution of glycosylation to the mobility of the natural protein. The deduced protein sequence corresponding to the mature protein contains 3 potential N-linked glycosylation sites with the sequence Asn-X-Thr/Ser (amino acid positions 145, 195, and 256). Amino acid sequence analysis of purified whole TFI and two isolated proteolytic fragments match exactly the protein sequence deduced from cDNA sequence (FIG. 3, underlined), indicating the isolated cDNA clone encodes TFI. The 3'-noncoding region is A+T rich (70% A+T). Neither consensus polyadenylation signal, AATAAA [Proudfoot and Brownlee, *Nature* 252, 359–362 (1981)] nor the poly A tail was found in this clone, possibly due to artefactual loss of part of 3' terminal portion during construction of the library.

Charge Distribution, Hydrophobicity/Hydrophilicity, and Internal Homology

The translated amino acid sequence of the TFI contains 27 lysines, 17 arginines, 11 aspartic acids, and 25 glutamic acids. The charge distribution along the protein is highly uneven as shown in FIG. 4. The signal peptide region contains 2 positively charged lysine with 26 neutral residues. The amino-terminal region of the mature protein contains a highly negatively charged stretch. Six of the first 7 residues are either aspartic acid or glutamic acid which are followed closely by two more negatively charged amino acids downstream before a positively charged lysine residue appears. The center portion of the molecule is generally negatively charged. At the carboxy terminal, there is a highly positively charged segment. The amino acids 265 to 293 of TFI contain 14 positively charged amino acids including a 6-consecutive arginine+lysine residues.

The predicted hydrophilicity/hydrophobicity profile of TFI protein is shown in FIG. 5. The signal peptide contains a highly hydrophobic region as expected. The rest of the molecule appears rather hydrophilic.

The translated amino acid sequence of TFI contains several discernible domains. Besides the highly negatively charged N-terminal domain and the highly positively charged C-terminal domain, the center portion consists of 3 homologous domains which have the typical sequences of the Kunitz-type inhibitors (see below).

Homology to Other Proteins

By searching the National Biomedical Research Foundation sequence data base, it was found that the N-terminal domain and C-terminal domain of TFI do not show significant homology to other known proteins. The 3 internal homologous domains, however, are each homologous to the sequences of other basic protease inhibitors including bovine pancreatic basic protease inhibitor (aprotinin), venom basic protease inhibitors, and inter-α-trypsin inhibitors (FIG. 6). It is noteworthy that disulfide bonding structure is highly conserved in all these inhibitors. Based on these homologies, it is clear that TFI belongs to the basic protease inhibitor gene superfamily.

Northern blotting

Poly(A)+ RNAs were purified from TFI-producing liver-derived cell lines, Chang liver, HepG2 hepatomaf and SK-HEP-1 hepatoma cells. The poly (A)+ RNAs were resolved by denaturing agarose gel electrophoresis, trans-blotted onto a nitrocellulose paper and probed with $^{32}$P-labeled TFI cDNA (λP9). As shown in FIG. 7, two major bands of hybridization were observed that corresponded to mRNAs of 1.4 kb and 4.4 kb in all three cell lines tested. Several other cell lines were tested which do not produce detectable amounts of TFI and in which no hybridization with the probe was found. (data not shown).

Various other examples will be apparent to the person skilled in the art after reading the present disclosure without departing from the spirit and scope of the invention. It is intended that all such further examples be included within the scope of the appended claims.

What is claimed is:

1. An isolated and purified antibody having a binding specificity for tissue factor inhibitor (TFI) having an amino acid sequence as shown in SEQ ID NO: 2.

2. The antibody of claim 1 which binds to a tissue factor inhibitor (TFI) region selected from the group consisting of
   (a) the N-terminal amino acids 1–27 or 3–25 of purified mature TFI as shown in SEQ ID NO: 2;
   (b) the C-terminal amino acids 237–265 of purified mature TFI as shown in SEQ ID NO: 2;
   (c) a V8 protease plus trypsin-digested peptide of TFI with the sequence of amino acids 54–60 as shown in SEQ ID NO: 2;
   (d) a V8 protease plus trypsin-digested peptide of TFI with the sequence of amino acids 125–138 as shown in SEQ ID NO: 2;
   (e) amino acids 26–76 or 19–89 of SEQ ID NO: 2 which form Kunitz domain 1 of TFI;
   (f) amino acids 97–147 or 90–160 of SEQ ID NO: 2 which form Kunitz domain 2 of TFI; and
   (g) amino acids 189–239 or 182–252 of SEQ ID NO: 2 which form Kunitz domain 3 of TFI.

3. The antibody of claim 1 which does not bind a polypeptide selected from the group consisting of bovine basic protease inhibitor precursor, bovine colostrum trypsin inhibitor, bovine serum basis protease inhibitor, edible snail isoinhibitor K, Red sea turtle basic protease inhibitor, Western sand viper venom basic protease inhibitor I, Ringhals venom basic protease inhibitor II, Cape cobra venom basic protease inhibitor II, Sand Viper venom basic protease inhibitor III, Eastern green mamba venom basic protease inhibitor I homologue, Black mamba venom basic protease inhibitors B, E, I, and K, β-1-bungarotoxin B chain (major); β-1-bungarotoxin B chain; Horse inter-α-trypsin inhibitor (amino acids 1–57 and 58–123), and Human α-1-microglobulin/inter-α-trypsin inhibitor precursor (amino acids 47–117, 118–188, and 210–280).

4. A composition comprising the antibody of 1, 2, or 3 and an effective carrier, vehicle or auxiliary agent.

5. A composition comprising the antibody of claim 1, 2, or 3 and a solution.

6. The antibody of claim 1, 2, or 3, wherein said antibody is a polyclonal antibody.

* * * * *